United States Patent
Akassoglou et al.

(10) Patent No.: US 10,451,611 B2
(45) Date of Patent: Oct. 22, 2019

(54) COMPOSITIONS AND METHODS FOR IN VITRO ASSAYS OF FIBRIN ACTIVITY

(71) Applicant: THE J. DAVID GLADSTONE INSTITUTES, San Francisco, CA (US)

(72) Inventors: Katerina Akassoglou, San Francisco, CA (US); Jae Kyu Ryu, San Francisco, CA (US); Anke Meyer-Franke, Menlo Park, CA (US)

(73) Assignee: THE J. DAVID GLADSTONE INSTITUTE, Redwood City, CA (US)

( * ) Notice: Subject to any disclaimer, the term of this patent is extended or adjusted under 35 U.S.C. 154(b) by 151 days.

(21) Appl. No.: 15/109,160

(22) PCT Filed: Jan. 9, 2015

(86) PCT No.: PCT/US2015/010775
§ 371 (c)(1),
(2) Date: Aug. 31, 2016

(87) PCT Pub. No.: WO2015/106072
PCT Pub. Date: Jul. 16, 2015

(65) Prior Publication Data
US 2016/0320370 A1    Nov. 3, 2016

Related U.S. Application Data

(60) Provisional application No. 61/926,313, filed on Jan. 11, 2014.

(51) Int. Cl.
*G01N 33/50* (2006.01)

(52) U.S. Cl.
CPC ..... *G01N 33/5058* (2013.01); *G01N 33/5055* (2013.01); *G01N 2333/70553* (2013.01); *G01N 2333/75* (2013.01)

(58) Field of Classification Search
None
See application file for complete search history.

(56) References Cited

U.S. PATENT DOCUMENTS

| 5,935,850 | A | 10/1999 | Clark | |
|---|---|---|---|---|
| 2005/0261472 | A1* | 11/2005 | Wescott | A61K 49/0032 530/328 |
| 2011/0166075 | A1 | 7/2011 | Akassoglou | |

FOREIGN PATENT DOCUMENTS

| WO | WO 1996004304 | 2/1996 |
|---|---|---|
| WO | WO 2001002855 | 1/2001 |
| WO | WO 2001009188 | 2/2001 |
| WO | WO 2011041518 | 4/2011 |

OTHER PUBLICATIONS

Midwood et al. (J Investigative Dermatology Symposium Proceedings 2006 vol. 11, p. 73-78 (Year: 2006).*
Cho et al. (J. Biol. Chem. 2005 vol. 280, p. 35490-35498). (Year: 2005).*
Kim et al. (J Biol. Chem. 2012 vol. 287, p. 4652-4661) (Year: 2012).*
Ariens et al. (Blood 2002 vol. 100, p. 742-754) (Year: 2002).*
Adams, R.A. et al. (2007) "Fibrinogen signal transduction as a mediator and therapeutic target in inflammation: lessons from multiple sclerosis"; *Current Medicinal Chemistry*, 14(27), p. 2925-2936.
Adams, R. A. et al. (2007) "The fibrin-derived γ 377-395 peptide inhibits microglia activation and suppresses relapsing paralysis in central nervous system autoimmune disease"; *J. Exp. Med.* 204; pp. 571-582.
Akassoglou, K., et al. (2002) "Fibrin inhibits peripheral nerve remyelination by regulating Schwann cell differentiation"; *Neuron* 33; pp. 861-875.
Akiyama, H. & McGeer, PL (1990) "Brain microglia constitutively express β-2 integrins"; *Journal of Neuroimmunology*, 30(1); pp. 81-93.
Bedard, K. & Krause, K. H. (2007) "The NOX family of ROS-generating NADPH oxidases: physiology and pathophysiology"; *Physiol. Rev.* 87; pp. 245-313.
Bugge, T. H. et al. (1996) "Loss of fibrinogen rescues mice from the pleiotropic effects of plasminogen deficiency"; *Cell* 87: pp. 709-719.
Chen, R. & Doolittle, R. F. (1971) "γ-γ cross-linking sites in human and bovine fibrin"; *Biochemistry* 10; pp. 4487-4491.
Davalos D et al. (2012) "Fibrinogen-induced perivascular microglial clustering is required for the development of axonal damage in neuroinflammation"; *Nat Commun.*;3: 1227; pp. 1-15.

(Continued)

Primary Examiner — Changhwa J Cheu
(74) Attorney, Agent, or Firm — Michael B. Rubin; Bozicevic, Field & Francis LLP

(57) ABSTRACT

The present invention provides compositions exhibiting in vivo activity of fibrin in an in vitro setting, in vitro assays comprising such compositions, methods of producing such compositions, and methods of using such compositions and assays. The compositions of the invention include molecules with the biochemical properties of 1) high affinity binding to fibrin receptors and 2) activation of cell-signaling systems comparable to that observed in vivo by fibrin. The fibrin compositions of the invention are compatible both in biochemical assays and cell-based assays, and thus useful for in vitro assays for screening of test agents that modulate cell activation and/or signaling pathways mediated by fibrin or associated with fibrin activity.

12 Claims, 8 Drawing Sheets

(56) References Cited

OTHER PUBLICATIONS

Dekosky, S. T. & Scheff, S. W. (1990) "Synapse loss in frontal cortex biopsies in Alzheimer's disease: correlation with cognitive severity"; *Ann. Neurol.* 27; pp. 457-464.

Fan, ST and Edgington, TS, 1(993) "Integrin regulation of leukocyte inflammatory functions CD11b/CD18 enhancement of the tumor necrosis factor-alpha responses of monocytes"; *Journal of Immunology* 150(7), pp. 2972-2980.

Flick, M. J. et al. (2004) "Leukocyte engagement of fibrin(ogen) via the integrin receptor α Mβ β2/Mac-1 is critical for host inflammatory response in vivo"; *J. Clin. Invest.* 113; pp. 1596-1606.

Frischer, J. M. et al. (2009) "The relation between inflammation and neurodegeneration in multiple sclerosis brains"; *Brain* 132: pp. 1175-1189.

Haider, L. et al. (2011) "Oxidative damage in multiple sclerosis lesions"; *Brain* 134; pp. 1914-1924.

Han, M. H. et al. (2008) "Proteomic analysis of active multiple sclerosis lesions reveals therapeutic targets"; *Nature* 451; pp. 1076-1081.

Koseki-Kuno, S., et al. (2003) "Factor XIII A subunit-deficient mice developed severe uterine bleeding events and subsequent spontaneous miscarriages"; *Blood* 102; pp. 4410-4412.

Lak, M., et al. (1999) "Bleeding and thrombosis in 55 patients with inherited afibrinogenaemia"; *British Journal of Haematology* 107; pp. 204-206.

Lassmann, H. (2011) "Mechanisms of neurodegeneration shared between multiple sclerosis and Alzheimer's disease"; *J. Neural Transm.* (Vienna) 118; pp. 747-752.

Marik, C.,et al (2007) "Lesion genesis in a subset of patients with multiple sclerosis: a role for innate immunity?"; *Brain* 130; pp. 2800-2815.

Midwood et al. (2006) "Modulation of Cell-Fibronectin Matrix Interactions during Tissue Repair"; *Journal of Investigative Dermatology Symposium Proceedings*, vol. 11; pp. 73-78.

Mócsai, A. et al. (2006) "Integrin signaling in neutrophils and macrophages uses adaptors containing immunoreceptor tyrosine based activation motifs"; *Nat. Immunol.* 7; pp. 1326-1333.

Neri, et al. (1995) "High-affinity antigen binding by chelating recombinant antibodies (CRAbs)"; *J Mal. Biol*, 246; pp. 367-373.

Nikić, I. et al. (2011) "A reversible form of axon damage in experimental autoimmune encephalomyelitis and multiple sclerosis"; Nat. Med. 17; pp. 495-499.

Oka, A., et al. (1993) "Vulnerability of oligodendroglia to glutamate: pharmacology, mechanisms, and prevention"; *J. Neurosci.* 13: pp. 1441-1453.

Park, L. et al. (2011) "Scavenger receptor CD36 is essential for the cerebrovascular oxidative stress and neurovascular dysfunction induced by amyloid-β. Proc"; *Natl. Acad. Sci. USA* 108; pp. 5063-5068.

Rivest, S. (2009) "Regulation of innate immune responses in the brain"; *Nat. Rev. Immunol.* 9; pp. 429-439.

Ryu, et al, (2009) "Fibrinogen signal transduction in the nervous system"; *J Thromb Haemost Suppl* 1:151-4. doi: 10.1111/j.1538-7836.2009.03438.x.

Schachtrup C, et al "Fibrinogen triggers astrocyte scar formation by promoting the availability of active TGF-beta after vascular damage"; *J Neurosci.* 2010 30(17); pp. 5843-5854.

Shimohama, S. et al. (2000) "Activation of NADPH oxidase in Alzheimer's disease brains"; *Biochem. Biophys. Res. Commun.* 273; pp. 5-9.

Smiley, ST. et al, (2001) "Fibrinogen stimulates macrophage chemokine secretion through toll-like receptor 4"; *Journal of Immunology*, 167(5), pp. 2887-2894.

Suh, T. et al. (1995) "Resolution of spontaneous bleeding events but failure of pregnancy in fibrinogen-deficient mice"; *Genes Dev.* 9; pp. 2020-2033.

Traunecker et al, (1991) "Bispecific single chain molecules (Janusins) target cytotoxic lymphocytes on HIV infected cells"; *Embo J* 10(12); pp. 3655-3659.

Turnbull, I. R. & Colonna, M. (2007) "Activating and inhibitory functions of DAP12"; *Nat. Rev. Immunol.* 7; pp. 155-161.

Ugarova, T. P. et al. (2003) "Sequence γ γ 377-395(P2), but not γ 190-202(P1), is the binding site for the alpha MI-domain of integrin α Mβ 2 in the γ C-domain of fibrinogen"; *Biochemistry* 42; pp. 9365-9373.

Ugarova, TP & Yakubenko, VP, (2001) "Recognition of fibrinogen by leukocyte integrins"; *Annals of the New York Academy of Sciences*, 936; pp. 368-385.

Van Oijen M. et al (2005) "Fibrinogen is associated with an increased risk of Alzheimer disease and vascular dementia."; *Stroke* 36(12); pp. 2637-2641.

Wu C et al. (2007) "Simultaneous targeting of multiple disease mediators by a dual-variable-domain immunoglobulin"; *Nat Biotechnol.* 25(11); pp. 1290-1297. Epub Oct. 14, 2007.

Xu Get al. (2008) "Plasma fibrinogen is associated with cognitive decline and risk for dementia in patients with mild cognitive impairment"; *Int J Clin Pract* 62(7); pp. 1070-1075.

\* cited by examiner

COMPOSITIONS AND METHODS FOR IN VITRO ASSAYS OF FIBRIN ACTIVITY

GOVERNMENT SUPPORT

This invention was made with government support under Grant NS052189 awarded by the National Institutes of Health. The government has certain rights in the invention.

FIELD OF THE INVENTION

The present invention relates to the field of compositions and in vitro assays for the identification of agents for the prevention and treatment of pathological conditions associated with neuronal injury.

BACKGROUND OF THE INVENTION

In the following discussion certain articles and methods will be described for background and introductory purposes. Nothing contained herein is to be construed as an admission of prior art. Applicant expressly reserves the right to demonstrate, where appropriate, that the articles and methods referenced herein do not constitute prior art under the applicable statutory provisions.

Fibrinogen is a key player in the coagulation cascade and has critical functions in the regulation of inflammation (Davalos and Akassoglou, Semin. Immunopathol. 2012 34(1):43-62). Although soluble fibrinogen in the bloodstream is not proinflammatory, its conversion to insoluble fibrin after activation of coagulation leads to exposure within the fibrinogen y chain of the cryptic epitope γ377_395, which binds to CD11b/CD18 integrin (Mac-1, complement receptor 3, aM~2) (Altieri et al., *J Biol Chem.* 1990 Jul. 25; 265(21):12119-22; Lishko et al., 2002; *Biochemistry.* 2002 Oct. 29; 41(43):12942-51.). Epitope exposure can occur during fibrin formation in vivo, or upon fibrinogen immobilization on substrates. However, there is no method described to efficiently reproduce the in vivo configurations of fibrin provided by its interactions with other molecules in vitro, or to predict the functional activity of an agent that binds to fibrin based on an in vitro assay.

There is thus a need in the art for a method of preparing fibrin compositions with the ability to predict functional utility using activity demonstrated in an in vitro setting. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides compositions exhibiting in vivo activity of fibrin in an in vitro setting, in vitro assays comprising such compositions, methods of producing such compositions, and methods of using such compositions and assays. The compositions of the invention include molecules with the biochemical properties of 1) high affinity binding to fibrin receptors and 2) activation of cell-signaling systems comparable to that observed in vivo by fibrin. The fibrin compositions of the invention are compatible both in biochemical assays and cell-based assays, and thus useful for in vitro assays for screening of test agents that modulate cell activation and/or signaling pathways mediated by fibrin or associated with fibrin activity.

The fibrin compositions and assays of the invention are useful in assessing the predicted in vivo activity of test agents identified as modulating fibrin-induced cell signaling and/or cell activation activity in an in vitro setting.

In one aspect, the invention provides an in vitro fibrin composition that displays high affinity binding to fibrin receptors and at least a two-fold increase in cell activation upon introduction of the composition to cells in vitro. Preferably, the composition displays between a 2- to 100-fold increase in cell activation upon introduction of the composition to cells in vitro.

Cell activation may be identified using a variety of biological end points, including but not limited to changes in cell size, changes in gene expression, ROS release, and changes in intracellular signaling pathways, such as signaling through NF-κB. In certain specific aspects, the cell activation is activation of an immune cell, e.g., a macrophage. In other specific aspects, the cell activation is activation of a cell of the central nervous system, e.g. a microglial cell. In other specific aspects, the cell activation is activation of CNS glia, such as oligodendrocytes or astrocytes. In other aspects, the cell activation is activation of endothelial cells, neurons, or neuronal precursors. In other aspects, cell activation can include non-CNS cells, such as cardiac, skin, liver, or stem cells.

The cellular activation displayed upon introduction, of the fibrin composition of the invention to a cell population of interest may be associated with an increase in gene expression. Alternatively or in addition, the cellular activation displayed upon introduction of the fibrin composition of the invention to a cell population of interest may be associated with an increase in reactive oxidative species. Alternatively or in addition, the cellular activation may be associated with changes in cell size or outgrowth of cell protrusions. Alternatively or in addition, the cellular activation may be associated with changes in intracellular signaling pathways, such as ERK1/2 or NF-κB. Alternatively or in addition, the cellular activation may be associated with changes in cell differentiation. Alternatively or in addition, the cellular activation may be associated with changes in protein expression either on the cell surface or secreted in the supernatants.

In certain embodiments, the invention provides an assay apparatus comprising a solid surface and a fibrin composition of the invention, where the fibrin composition is adhered to the support surface. The support surface to which the fibrin composition is immobilized may be any solid substance to which fibrin will adhere. Preferably, the solid substrate is glass, polyethylene, polystyrene or a cyclic olefin polymer substrate.

In specific embodiments, the invention provides a research tool for the identification of agents that modulate in vivo fibrin activity, comprising a fibrin composition that displays high affinity binding to fibrin receptors and at least a two-fold, and preferably between a 2 to 100 fold increase in cell activation upon introduction of the composition in vitro to cells of the neuronal lineage.

In other embodiments, the invention provides an assay method for identification of test agents that induce cell activation, comprising immobilizing a fibrin composition of the invention to a solid support surface, introducing cells of a neuronal lineage to the solid support surface, and measuring one or more biological outputs associated with the activation of the cell. In certain aspects the cells activated are cells of the central nervous system. In other aspects the cells activated are immune cells. The biological outputs that can be measured in these assays include, but are not limited to, expression of one or more genes known to be associated with activation of the cells, and the production of a reactive oxidative species associated with activation of the cells.

In still other embodiments, the invention provides assay methods for identification of test agents that modulate CD11b signaling through fibrin, comprising the steps of immobilizing a fibrin composition of claim 1 to a solid support surface, introducing the test agent to the support surface, measuring the binding affinity of the test agent to the fibrin composition immobilized on the solid support surface, and identifying agents that exhibit a high binding affinity to the fibrin composition in vitro.

In yet other embodiments, the invention provides assay methods for identification of an agent for modulation of a biological process involving signaling through fibrin, said method comprising providing a research tool comprising a fibrin composition of the invention adhered to a solid surface, testing one or more binding partners for modulation of functional activity of the fibrin in the research tool composition, and isolating the binding partners that display the desired change in functional activity of the research tool composition. The binding partners that display the desired change in functional activity of the research tool composition are confirmed as candidates agents for modulation of a biological process associated with signaling through fibrin.

Such candidate agents may be particularly useful in clinical applications for conditions involving impaired immune function, e.g., diseases associated with autoimmunity such as multiple sclerosis or rheumatoid arthritis, or conditions associated with neuronal injury, e.g., neurodegeneration associated with aging, neurodegenerative diseases, and trauma (e.g., ischemia).

In one aspect, the invention provides methods to prepare in vitro fibrin that mimics the biochemical and proinflammatory properties of the fibrin matrices found in vivo.

In another aspect, the invention provides an apparatus comprising the fibrin composition of the invention for use in assay systems.

In yet another aspect, the invention provides methods of producing the fibrin compositions, apparatus comprising such fibrin compositions and research tools comprising such fibrin compositions.

In yet another aspect, the invention provides assay systems that use the fibrin compositions of the invention.

These and other aspects, features and advantages will be provided in more detail as described herein.

DETAILED DESCRIPTION OF THE INVENTION

Figure 1:
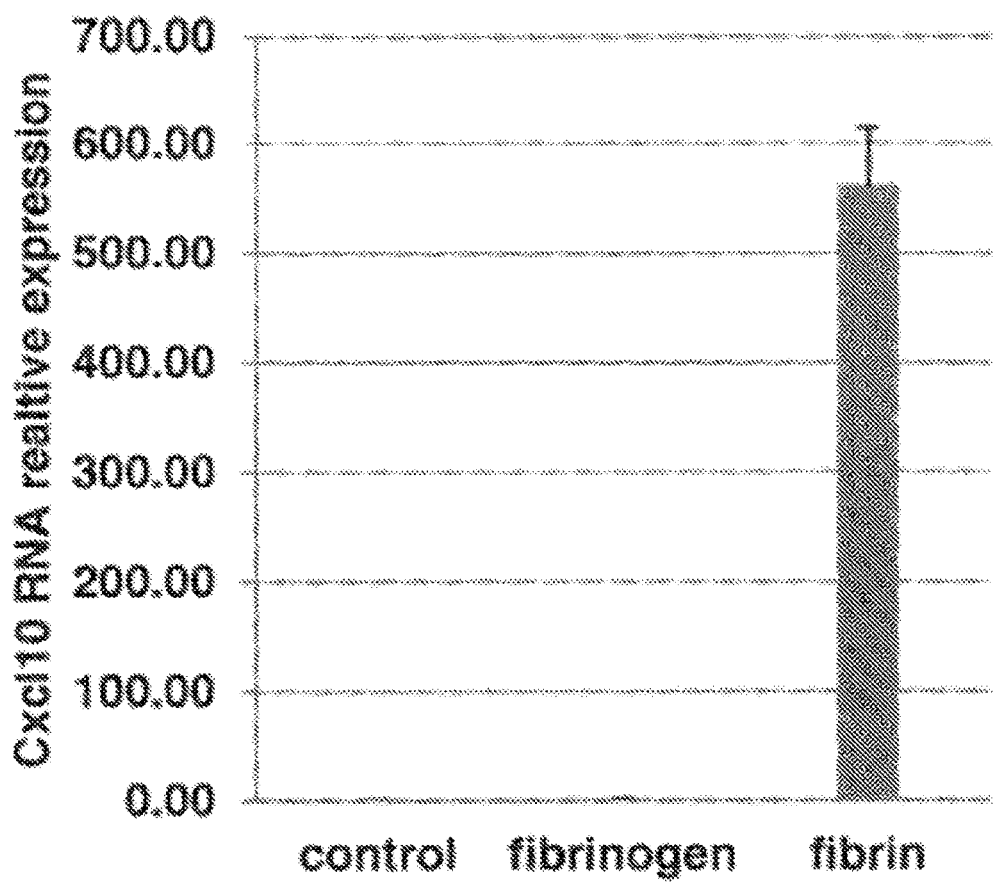
FIG. 1 is a graph illustrating the expression of Clcx10 mRNA in a first assay system of the invention comprising the use of bone marrow derived macrophages (BMDMs).
Figure 2:
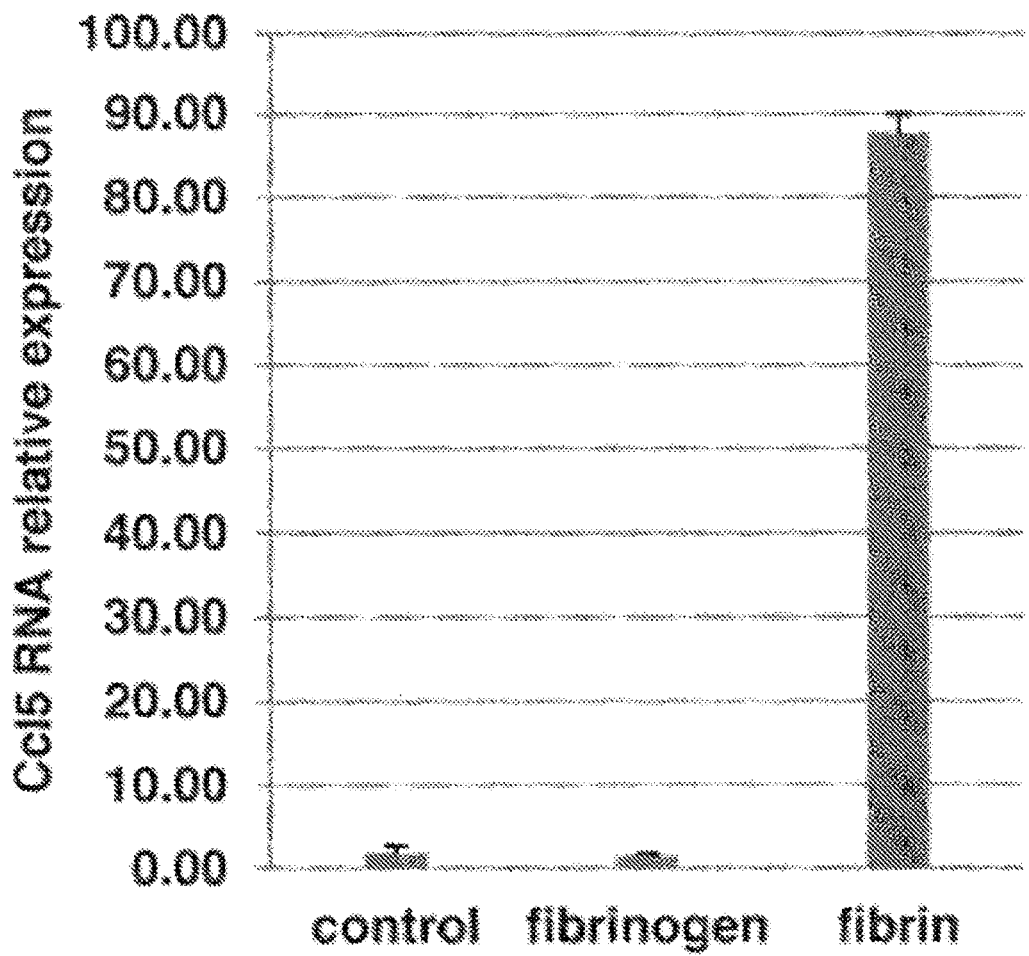
FIG. 2 is a graph illustrating the expression of Ccl5 mRNA in a first assay system of the invention comprising the use of BMDMs.
Figure 3:
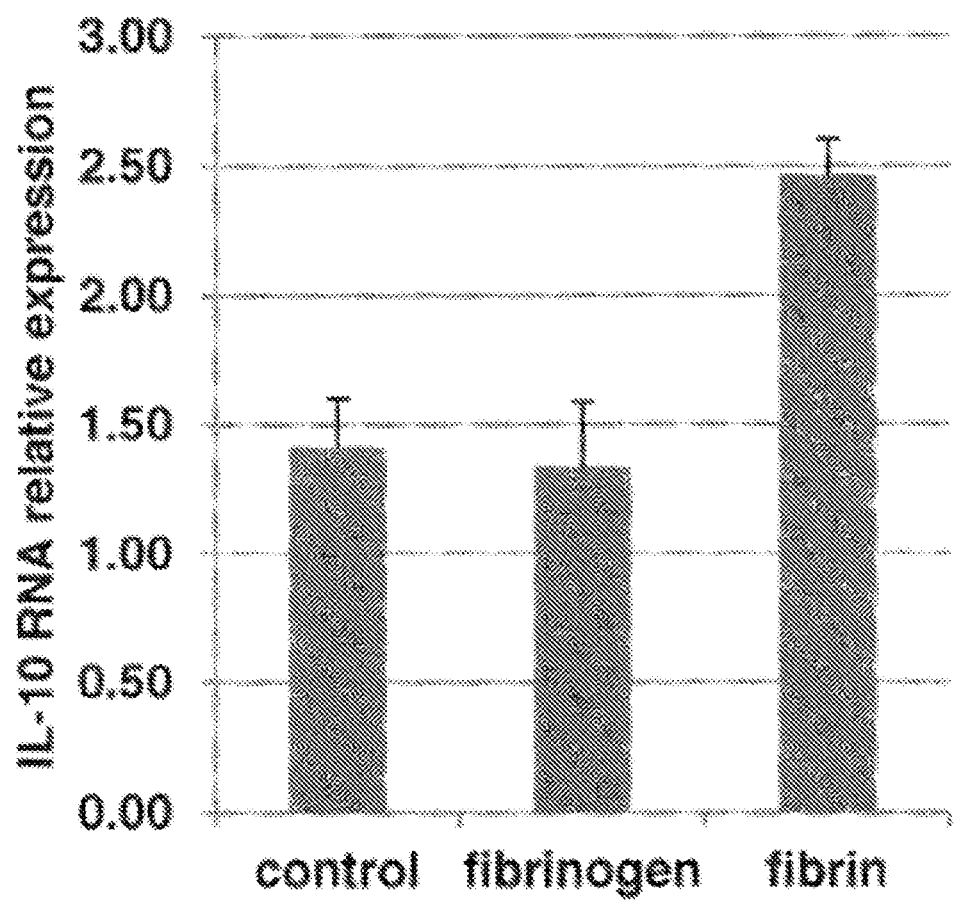
FIG. 3 is a graph illustrating the expression of I1-10 mRNA in a first assay system of the invention comprising the use of BMDMs.
Figure 4:
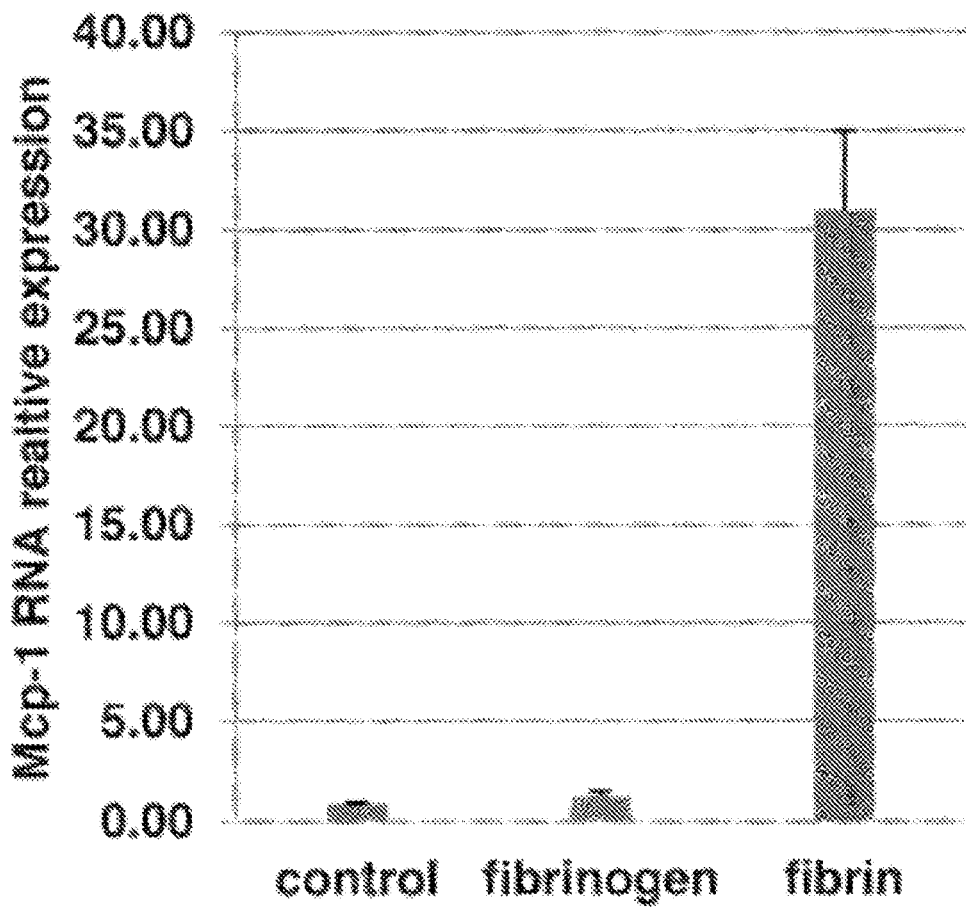
FIG. 4 is a graph illustrating the expression of Mcp-1 mRNA in a first assay system of the invention comprising the use of BMDMs.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Harlow and Lane, *Antibodies, A Laboratory Manual*, Cold Spring Harbor Publications, New York, 1988; Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Lehninger, *Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "a test agent" refers to one, more than one, or mixtures of such agents, and reference to "a method" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The term "antibody" is intended to include any polypeptide chain-containing molecular structure with a specific shape that fits to and recognizes an epitope, where one or more non-covalent binding interactions stabilize the complex between the molecular structure and the epitope. As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Where bispecific antibodies are to be used, these may be conventional bispecific antibodies, which can be manufactured in a variety of ways (Bolliger and Winter, *Curr Opin Biotechnol.* 1993 4(4):446-9), e.g., prepared chemically or from hybrid hybridomas, or may be any of the bispecific antibody fragments mentioned above. It may be preferable to use scFv dimers or diabodies rather than whole antibodies. Diabodies and scFv dimers can be constructed without an Fc region, using only variable domains, potentially reducing the effects of anti-idiotypic reaction. Other forms of bispecific antibodies include the single chain "Janusins" described in Traunecker et al, *Embo J.* (1991) 10(12):3655-9. Such antibodies also include CRAbs, which are chelating antibodies which provide high affinity binding to an antigen, D. Neri, et al. *J. Mol. Biol,* 246, 367-373, and dual-variable domain antibodies as described in Wu C et al., *Nat Biotechnol.* 2007 November; 25(11):1290-7. Epub 2007 Oct. 14.

The term "diagnostic tool" as used herein refers to any composition or assay of the invention used in order to carry out a diagnostic test or assay on a patient sample. As a diagnostic tool, the composition of the invention may be considered an analyte specific reagent, and as such may form part of a diagnostic test regulated by a federal or state agency. The use of the compositions of the invention as a diagnostic tool is not intended to be related to any use of the composition in the development of therapeutic agents.

The term "microglial activation" as used herein can refer to processes associated with innate activation or adaptive activation of the microglia. Such activation may include morphological changes of the microglial cells, including shortening of cellular processes and enlargement of their soma, as well as the release of proinflammatory cytokines and chemokines, reactive oxygen and/or nitrogen intermediates, proteinases and complement proteins, and upregulation of cell surface activation antigens.

The term "neurodegeneration" refers to a physiological state caused by neuronal injury associated with neuronal loss and/or damage. In specific aspects, neurodegeneration refers to neuronal injury resulting in impaired cognitive function.

The term "neuronal injury" as used herein refers to any damage or dysfunction exhibited by neurons, including but not limited to loss of myelin, dendrite retraction, dendritic spine density reduction, axonal damage and neuronal death.

A "neuronal condition" as used herein refers to any damage or dysfunction exhibited by neurons, including but not limited to dendrite retraction, dendritic spine density reduction, axonal damage and neuronal death. The term "pharmaceutically acceptable carrier" as used herein is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents is well known in the art. Except insofar as any conventional media or agent is incompatible with the agents provided herein, use thereof in the composition is contemplated.

The terms "peptide," "polypeptide," and "protein" are used interchangeably herein, and refer to a polymeric form of amino acids of any length, which can include coded and non-coded amino acids, chemically or biochemically modified, labeled or derivatized amino acids, and polypeptides having modified peptide backbones.

The term "peptidomimetic" as used herein refers to a protein-like chain designed to mimic a peptide. They typically arise from modification of an existing peptide in order to alter the molecule's properties. For example, they may arise from modifications to change a molecule's stability, biological activity, or bioavailability.

The term "pharmacophore" is used herein in an unconventional manner. Although the term conventionally means a geometric and/or chemical description of a class or collection of compounds, as used here the term means a compound that has a specific biochemical activity or binding property conferred by the 3-dimensional physical shape of the compound and the electrochemical properties of the atoms making up the compound. Thus, as used here the term "pharmacophore" is a compound and not a description of a collection of compounds which have defined characteristics. Specifically, a "pharmacophore" is a compound with those characteristics.

The term "small molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

"Solid support" and "support" are used interchangeably and refer to a material or group of materials having a rigid or semi-rigid surface or surfaces.

The term "research tool" as used herein refers to use of any animal model or assay of the invention for scientific enquiry, whether academic or commercial in nature, including the identification and development of candidate therapeutic agents. The research tools of the invention are not themselves intended to be therapeutic or to be subject to regulatory approval; rather, the research tools of the invention are intended to facilitate research and aid in such development activities, including any activities performed with the intention to produce information to support a regulatory submission.

A "test agent" as used herein refers to any agent that is a candidate to treat a disease or symptom thereof. Such agents include, but are not limited to, peptides; proteins (including derivatized or labeled proteins); antibodies or fragments thereof; small molecules; aptamers; carbohydrates and/or other non-protein binding moieties; derivatives and fragments of naturally-occurring binding partners; peptidomimetics; and pharmacophores.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in an animal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The Invention in General

The present invention is based on the novel development of a composition that mimics the biochemical and proinflammatory properties of fibrin matrices found in vivo during pathological conditions in an in vitro setting. These fibrin compositions are highly reproducible in activity, and provide the advantage of essentially mimicking the in vivo activity of fibrin, and use of such compositions in assays enable the screening of fibrin inhibitors that have a higher likelihood of being efficacious in clinical use. More particularly, by using a fibrin composition with similar properties of fibrin in vivo activity observed in pathological conditions, the probability of finding biologically active inhibitors with in vivo efficacy is enhanced.

Assays using the fibrin compositions of the invention are useful in high throughput screening applications, including assays to screen small molecules and antibody libraries for activity that modulates fibrin activity in vivo. In addition, the assays of the invention can be used to identify biomarkers indicative of fibrin-mediated pathological conditions, e.g., biomarkers present in the serum or cerebral spinal fluid (CSF) of a patient tested for a fibrin-mediated pathological condition. In certain embodiments, the assays of the invention can include other biological molecules that may enhance or reduce fibrin activity. Such biological molecules can include, but are not limited to, isolated fibrinogen, including fibrinogen that has undergone post-translational modifications, such as citrullination or nitrosylation.

The invention also provides methods to prepare fibrin compositions that mimic the biochemical and proinflammatory properties of the fibrin matrices found in vivo during pathological conditions. The method of fibrin preparation is highly reproducible. The assays described here are also superior to any other in vitro assay preparations available in terms of reproducibility and biochemical properties of high affinity binding to fibrin receptors and/or signaling through fibrin, as well as at least a two-fold, and preferably between a 2 to 100 fold increase of cell activation.

The fibrin compositions of the invention provide assays with the ability to induce a significant increase in assay end points such as measured increases in cell signaling activity and/or gene expression. For example, the fibrin compositions of the invention can increase gene expression in neuronal cells such as macrophages. The fibrin compositions of the present invention can also induce ROS release in macrophages in a CD11b-dependent manner. These results indicate that fibrin is responsible for the in vivo activity of fibroinogen-mediated cell activation, and thus immobilized fibrin is the primary in vitro bioactive and proinflammatory substrate in the cell activation assays of the invention.

Fibrin and Fibrinogen Signaling Systems

Fibrin and fibrinogen have been shown to have a vast signaling capacity with involvement in inflammatory mechanisms of a wide range of disorders including rheumatoid arthritis, sepsis, myocardial infarction, infection and multiple sclerosis (MS) (Adams, R. A. et al., 2007, *Current Medicinal Chemistry*, 14(27), p. 2925-36). These broad receptor signaling activities leading to various physiological reactions and differential induction of cytokines and chemokines suggest that fibrinogen and its proteolytic product fibrin may be able to promote diverse responses during different stages of inflammation as well as having a role in the inhibition of adult neurogenesis. Fibrinogen and/or fibrin have been implicated in the interaction with an array of receptors on differing cell types, and thus the fibrin compositions, assay methods, apparatus and research tools of the invention are useful in identifying test agents that have activity in the various signaling pathways that are associated with fibrin activity.

The CD11b/CD18 ($\alpha M\beta 2$, or MAC-1) receptor is a member of the $\beta$-integrin family of receptors and controls the innate immune response by regulating phagocyte adhesion, migration and engulfment of potentially harmful factors (Ehlers, M R W., 2000 *Microbes and Infection*, 2(3), pp. 289-294). The receptor is expressed on microglia cells, and upregulation has been observed in the brains of post mortem Alzheimer's disease patients (Akiyama, H. & McGeer, P L, 1990. *Journal of Neuroimmunology*, 30(1), pp. 81-93.). The association of fibrinogen with CD11b/CD18 on many immune cells suggests an important role for fibrin-mediated receptor activity in inflammatory responses. Fibrinogen-mediated TNFα release in isolated peripheral blood monocytes was dependent on CD11b (Fan, S T and Edgington, T S, 1993, *Journal of Immunology* 150(7), pp. 2972-80). Furthermore, fibrinogen treatment of the human monocytic cell line U937 induced significant IL-1β expression via CD11b and NFκB signalling (Perez et al. 1999, supra). Finally, blocking fibrin formation with anticoagulant treatment or genetically eliminating the fibrinogen binding motif recognized by the microglial integrin receptor CD11b/CD18 inhibits perivascular microglial clustering and axonal damage. Davalos D et al., *Nat Commun*. 2012; 3:1227.

Another integrin receptor CD11c/CD18, has been shown to interact with fibrinogen in the activation of dendritic cells (Ugarova, T P & Yakubenko, V P, 2001. *Annals of the New York Academy of Sciences*, 936, pp. 368-85). Studies using primary peritoneal macrophages have also shown fibrinogen can induce chemokine secretion via toll-like receptor 4 (TLR4) (Smiley, S T. et al., *Journal of Immunology*, 167(5), pp. 2887-2894). High plasma levels of fibrinogen have been linked to the onset of dementia and increase the risk of AD (Xu G et. al. *Int J Clin Pract* 62(7): 1070-1075; van Oijen M et. al., *Stroke* 36(12): 2637-2641). Fibrinogen has also been associated with the $\alpha v\beta 3$ integrin receptor, causing inhibition of neurite outgrowth via phosphorylation of the epidermal growth factor (EGF) receptor (Schachtrup C et al., 2010. *Journal of Neuroscience*, 30(17), pp. 5843-5854.). Fibrinogen has been shown to serve as an early signal in glial scar formation via the TGFβ/Smad signaling pathway in astrocytes. Schachtrup, C. et al., 2010. Id.

Test Agents for Screening Using the Compositions and Apparatus of the Invention

The fibrin compositions of the invention are useful as either research or diagnostic tools in functional assays, including: assays used to understand physiological processes; assays to identify new binding partners (including drug candidates) that selectively bind to fibrin signaling complexes and modulate specific signaling processes; and assays to test known compounds (including synthetic, recombinant or naturally-occurring compounds) for their effect on signaling through the fibrinogen/fibrin pathways, and the like. It is known in the pharmaceutical arts that binding affinity to a target and efficacy do not necessarily correlate, and that identification of functional changes conferred by a binding partner is a much better predictor of efficacy than binding affinity alone. The fibrin compositions of the invention are especially powerful in identification of binding partners with functional activity rather than just affinity, as the compositions not only can recreate functional activity of fibrin but also provide potentiation of the signaling pathway through interaction of the fibrin and at least one binding partner.

The assays for use with the compositions of the present invention include biochemical assays which can be correlated with in vivo efficacy for a physiological process, ex vivo cell-based assays for measurement of a physiological process, in vivo assays for direct or indirect measurement of a physiological process, etc.

The assays of the invention correlate with in vivo modulation of signaling through activated fibrin. Examples of cell-based assays for use with the present invention include, but are not limited to, high throughput binding screening; assays to measure cell activation, proliferation, necrosis and/or apoptosis; flow cytometry assays; metabolic assays measuring labeling or turnover; phase and fluorescence microscopy; receptor phosphorylation and/or turnover; cell signaling assays; immunohistochemistry studies; reporter gene assays, and subcellular fractionation and localization. More specific examples of such assays are: FLIPR to detect changes in intracellular calcium concentration and cell-based ELISA assays to detect and quantify cellular proteins including post-translational modifications associated with cell activation.

Biochemical assays can also be used to correlate binding with efficacy in the methods of the invention. These include, but are not limited to, spectrophotometric assays, fluorometric assays, calorimetric assays, chemiluminescent assays, radiometric assays, chromatographic assays, colorimetric assays, and substrate specificity inhibitor kinase assays. Specific examples are: luciferase assays, in which firefly luciferase protein catalyzes luciferin oxidation and light is generated in the reaction, and which is frequently used as a reporter gene for measuring promoter activity or transfection efficiency; electrophoresis; gas-liquid chromatography; and Forster resonance energy transfer (FRET).

In a specific aspect, in vitro assays are utilized to provide a correlation of binding affinity with efficacy in modulating a target. Examples of in vivo functional assays are radiolabelling assays, fluorescent protein expression assays, in vivo capture assays, NMR spectroscopy, or assays specifically designed to identify efficacy in an animal model of a pathological process.

For example, in treatment of certain diseases or disorders, therapeutics need to be initially tested in in vivo models due to the complex physiological parameters involved with efficacy.

The fibrin composition of the invention may also be used as a diagnostic tool to detect the presence or absence of molecules associated with a fibrin-mediated biological process in a patient.

Thus, in one aspect, the invention includes research tools comprising the compositions of the invention, and uses of such research tools in identification, investigation and/or confirmation of activity of test agents that may be useful as therapeutic agents. These research tools are generally useful before the inception of a plan for the clinical development of a test agent in the treatment of a fibrin-associated condition. The research tools of the invention provide for the identification and/or confirmation of the functional activity of an agent with fibrin binding sites.

Use of the research tools of the invention can in essence recreate one or more functional fibrin interactions that occur in vivo in a biological process (e.g., binding of fibrin to CD11b/CD18), thus potentiating selective binding of test agents that will have in vivo activity. It is known in the pharmaceutical arts that binding affinity to a target and in vivo modulation of a target do not necessarily correlate, and that identification of functional changes conferred by a binding partner is a much better predictor of efficacy than binding affinity alone. The fibrin compositions of the invention are especially powerful in identification of test agents with functional activity rather than just affinity to fibrin or fibrinogen.

The compositions and apparatus of the present invention are significantly advantageous over existing in vitro assays for functional fibrin activity, as they provide the ability to screen for inhibitors using a proinflammatory substrate with similar properties as the one found in disease, therefore increasing the probability of identifying inhibitors with in vivo efficacy.

Moreover, the assays are reproducible and thus appropriate for high throughput screening. For example, the assays can also be used to screen small molecule and antibody libraries, and used for biomarker screening for autoantibodies in serum or CSF of patients. The plates can be stored in −20° C. until use allowing for scale up of screening plates and quality controls for HTS.

The assay can be modified to include preparations of purified fibrinogen, fibrinogen depleted from growth factors or IgG, or fibrinogen that has undergone post-translational modifications, such as citrullination or nitrosylation. The assay can also be used to screen antibody libraries for identifying fibrin-specific antibodies.

To confirm the functional activity of a test agent, a therapeutically effective amount of a test agent of the invention may be administered to a subject (including an animal model of a neurological pathology) to confirm its in vivo activity following identification in an assay of the invention. By "therapeutically effective dose or amount" or "effective amount" is meant an amount of the test agent that, when administered, brings about a positive therapeutic response with respect to neuronal injury. In some embodiments of the invention, the therapeutically effective dose is in the range from about 0.1 g/kg to about 100 mg/kg body weight, about 0.001 mg/kg to about 50 mg/kg, about 0.01 mg/kg to about 30 mg/kg, about 0.1 mg/kg to about 25 mg/kg, about 1 mg/kg to about 20 mg/kg, about 3 mg/kg to about 15 mg/kg, about 5 mg/kg to about 12 mg/kg, about 7 mg/kg to about 10 mg/kg or any range of value therein. It is recognized that the method of treatment may comprise a single administration of a therapeutically effective dose or multiple administrations of a therapeutically effective dose.

The test agent is administered to supply a desired therapeutic dose to promote a desired therapeutic response of the modulator to the therapeutic area. By "desired therapeutic response" is intended an improvement in the condition or in the symptoms associated with the condition, including the inhibition of angiogenesis.

The test agents can be formulated in a unit dosage such as a solution, suspension or emulsion, in association with a pharmaceutically acceptable carrier. Such carriers are inherently nontoxic and nontherapeutic. Examples of such carriers are saline, Ringer's solution, dextrose solution, and Hanks' solution. Nonaqueous carriers such as fixed oils and ethyl oleate may also be used. The vehicle may contain minor amounts of additives such as substances that enhance chemical stability, including buffers and preservatives.

Various methods of delivery can be used to deliver the test agent, and will in part be dependent upon the agent and its bioavailability. For example, small molecules or other agents that are bioavailable may be administered orally, whereas protein-based agents are generally but not exclusively administered parenterally. Certain agents may be administered systemically, while others may be more beneficial with a local delivery. The method of delivery will be apparent to one skilled in the art upon reading the specification, and can be determined in view of the specific properties of the test agent.

It is understood that the effective amount of a test agent may vary depending on the nature of the effect desired, frequency of treatment, any concurrent treatment, the health, weight of the recipient, and the like. See, e.g., Berkow et al., eds., *Merck Manual,* 16th edition, Merck and Co., Rahway, N.J. (1992); Goodman et al., eds., *Goodman and Oilman's The Pharmacological Basis of Therapeutics,* 8th edition, Pergamon Press, Inc., Elmsford, N.Y. (1990); *Avery's Drug Treatment. Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston (1985), Katzung, *Basic and Clinical Pharmacology,* Appleton and Lange, Norwalk, Conn. (1992), which references and references cited therein, are entirely incorporated herein by reference.

The test agent may be contained in a pharmaceutically-acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and agents for delivering cells is well known in the art. Except insofar as any conventional media or agent is incompatible with the cells or polypeptides provided herein, use thereof in the compositions is contemplated. Supplementary active compounds can also be incorporated into the test agents.

For confirming in vivo activity, a composition comprising a test agent is formulated to be compatible with its intended route of administration. Examples of routes of administration include intravenous, intraarterial, intracoronary, parenteral, subcutaneous, subdermal, subcutaneous, intraperitoneal, intraventricular infusion, infusion catheter, balloon catheter, bolus injection, direct application to tissue surfaces during surgery, or other convenient routes.

Solutions or suspensions used for such administration can include other components such as sterile diluents like water for dilution, saline solutions, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The composition can be enclosed in ampoules, disposable syringes or multiple dose vials made of glass or plastic.

Test agents suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent possible. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents.

Prolonged absorption of the injectable compositions can be brought about by including in the composition an agent which delays absorption, for example, aluminum monostearate and gelatin. Sterile injectable solutions can be prepared by incorporating an active agent in the required amount in an appropriate solvent with a selected combination of ingredients, followed by filter sterilization. Generally, dispersions are prepared by incorporating an active agent into a sterile vehicle that contains a basic dispersion medium and the required other ingredients from those enumerated above. In the case of sterile powders for the preparation of sterile injectable solutions, methods of preparation are vacuum drying and freeze-drying that yield a powder of the active ingredient plus any additional desired ingredient from a previously sterile-filtered solution thereof. In many cases, it will be preferable to include isotonic agents.

Fibrin Assay Apparatus

The fibrin compositions of the invention can be used to create various configurations of apparatus for use in fibrin-mediated assays. In the assay apparatus of the invention, the fibrin compositions are immobilized onto various solid supports.

In many embodiments, at least one surface of the solid support will be substantially flat, although in some embodiments it may be desirable to physically separate regions on the support with, for example, wells. Multiple different configurations can be used for the adhesion of the fibrin compositions of the invention, and can be tailored based on the desired assay methodology and/or instrumentation.

The solid upon which the fibrin composition is supported is not limited to a particular substrate. Various solid supports, including glass-based and plastic-based, allow the solid support to be adapted to suit any particular assay. Solids which may be of use in this invention thus include, but are not limited to, silica-based substrates, such as glass, fused silica and other silica-containing materials and plastic materials such as polyethylene, polystyrene, poly(vinyl chloride), polypropylene, nylons, polyesters, polycarbonates and poly (methyl methacrylate). Preferred plastics materials are polyethylene, polystyrene and cyclic olefin polymer substrates. Alternatively, other solid supports may be used such as gold, titanium dioxide, or silicon supports.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Production of an Apparatus Comprising the Fibrin Composition of the Invention Fibrinogen solution was prepared using plasminogen-depleted fibrinogen from human plasma (Calbiochem) in cell culture grade dissolved in endotoxin-free HyClone™ water (ThermoFisher, Waltham, Mass.) to a final concentration of 25 mg/ml. The fibrinogen solution was prepared at 37° C., swirling every 30 minutes. The fibrinogen solution was added to a 20 µM HEPES-buffered saline solution to make a 20 µg/ml fibrinogen solution. The solution was stored in 1 ml aliquots at −80° C. until use.

A thrombin solution was prepared using the HEPES dissolved in 0.9% saline to a concentration of 1 M. Thrombin (1 KU) was dissolved in 1 ml HyClone™ water, and stored in 20 µl aliquots at 80° C. A $CaCl_2$ solution was created by dissolving $CaCl_2$ in HyClone water to a concentration of 0.7M $CaCl_2$.

In a separate tube, $CaCl_2$ solution was added to a 20 µM HEPES-buffered saline solution to a 1.4 µM final concentration. The thrombin solution was added to the $CaCl_2$ solution to create a solution with 2 U/ml of thrombin.

A fibrinogen assay plate was created by dispensing 50 µl of 20 µM HEPES-buffered saline solution in each well of a 96-well plate (NUNC MaxiSorp). 50 µl of 20 µg/ml fibrinogen solution was added into wells containing HEPES-buffered saline.

A fibrin assay plate was created by dispensing 50 µl of 20 µM HEPES-buffered saline solution containing $CaCl_2$ and thrombin in each well of a 96-well plate (NUNC MaxiSorp). 50 µl of the 20 µg/ml fibrinogen solution was added into wells containing HEPES-buffered saline with $CaCl_2$ and thrombin. The plate was sealed with adhesive seal against evaporation and incubated at 37° C. for 1 hr. After incubation, the seal was removed and the plates stored overnight in a drying chamber at 37° C. Following incubation, the plates were sealed with adhesive seal and stored at −20° C. or 4° C.

Example 2: Use of Fibrin Composition in an In Vitro Gene Expression Assay

To compare pro-inflammatory effects of fibrinogen and fibrin on macrophage activation, a chemokine gene expression assay was performed on cultured bone marrow derived macrophages (BMDMs) in fibrinogen- and fibrin-coated plates. Fibrin and fibrinogen assay plates were prepared as generally described in Example 1. The wells of each assay plate were coated with 100 µg/ml fibrinogen or 100 µg/ml fibrin. An uncoated 96-well plate was also used to serve as a negative control.

Approximately 100,000 BMDMs were plated per well on the fibrin assay plate, the fibrinogen assay plate, and the control plate. The plates were allowed to incubate for 6 hours at room temperature. Following incubation, real time PCR analysis expression using isolated mRNA from the BMDMs was performed. The results of the gene expression are summarized in FIGS. 1-4. The expression of Clcx10, Ccl5, Il-10 and Mcp-1 mRNA was significantly elevated in the fibrin assay plates compared to the mRNA of both the negative control plates and the fibrininogen assay plates. This demonstrates that the fibrin composition in the fibrin assay plates was able to stimulate a gene expression response in macrophages that is significantly higher than that seen by exposure of the macrophages to fibrinogen.

Example 3: Detection of Reactive Oxygen Species Using the Fibrin Composition in an In Vitro Assay One of the most invariant features of activated microglia and macrophages is the production of reactive-oxygen species (ROS). Thus, the generation of ROS by these cells is a reliable indicator of their activation.

To demonstrate that the fibrin composition of the invention had the ability to generate ROS in vitro, and thus activate microglia and/or macrophages, the fibrin assay plates produced using the methods of Example 1 were tested for their ability to induce ROS from BMDMs.

The chemical dihydroethidium (DHE) is oxidized specifically by superoxide anions, and the oxidized dye fluoresces red. By measuring the intensity of fluorescent signals in the wells produced by the oxidation of DHE, the amount of superoxide produced in the wells can be deduced. To investigate the ability of the fibrin compositions of the invention to activate macrophage, and thus to cause the release of ROS, BMDMs were exposed to fibrin assay plates comprising the fibrin compositions of the invention.

In addition, preliminary evidence suggests that at least some fibrin signaling activity may be through CD11b/CD18 receptor activation by fibrin-induced ROS. To investigate this, BMDMs were also incubated in the fibrin assay plates in the presence of an anti-CD11b antibody with the ability to block signaling through CD11b.

Fibrin assay plates were created by dispensing 50 µl of 20 µM HEPES-buffered saline solution containing $CaCl_2$ and thrombin in each well of a 96-well plate (NUNC MaxiSorp). 50 µl of the 20 µg/ml fibrinogen solution was added into wells containing HEPES-buffered saline with $CaCl_2$ and thrombin. The plate was sealed with adhesive seal against evaporation and incubated at 37° C. for 1 hr. After incubation, the seal was removed and the plates stored overnight in a drying chamber at 37° C. Following incubation, the plates were sealed with adhesive seal and stored at −20° C. or 4° C.

BMDMs were preincubated with 10 µM DHE for 30 min and then plated in the fibrin assays plates, or a control uncoated 96-well plate. A portion of these BMDMs were also incubated with either 10 µg/ml anti-Mac1 (CD11b/CD18) antibody or 10 µg/ml IgG2b. BMDMs were incubated with antibodies for 30 min at room temperature prior to fibrin exposure. After 30 min antibody incubation, cells were removed from the plate by PBS+0.04% EDTA.

Figure 5:
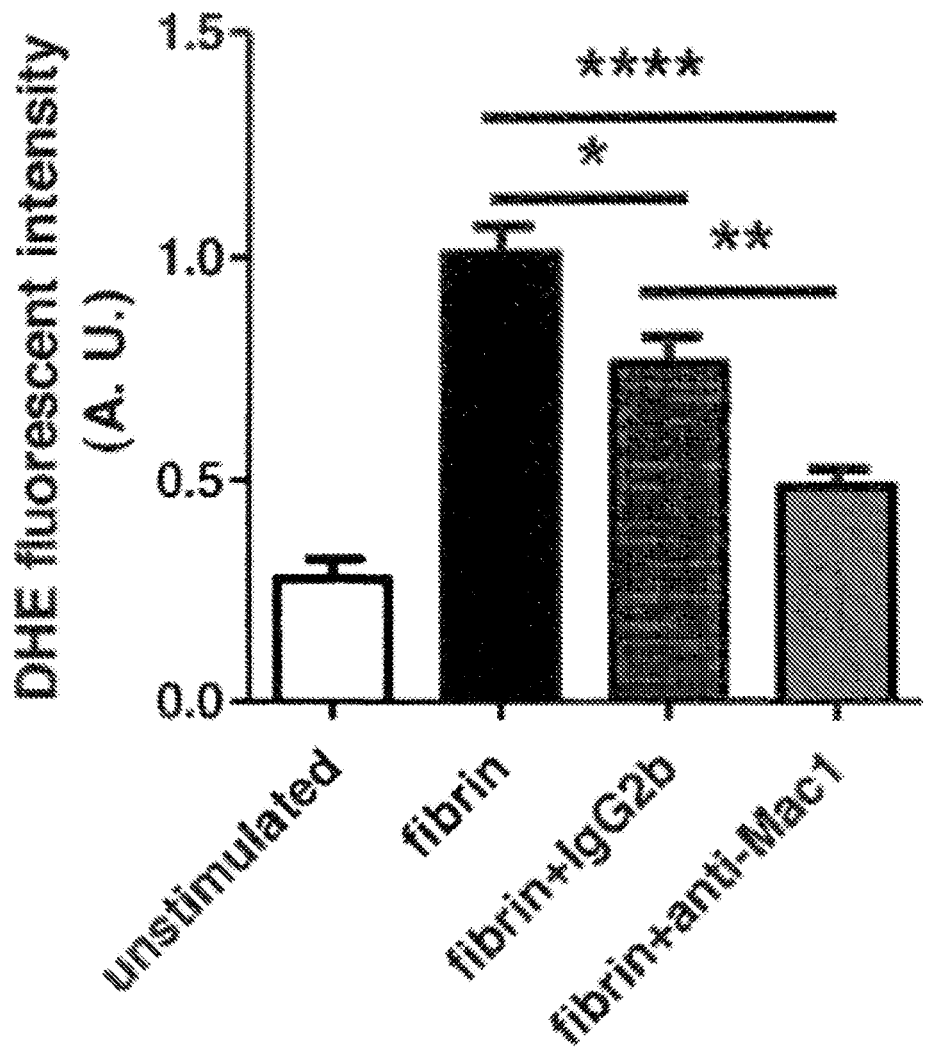
FIG. 5 is a graph illustrating the levels of reactive oxygen species resulting from dihydroethidium (DHE) oxidation in macrophages after 24 hours exposure to the fibrin composition of the invention, alone or with IgG2b or anti-Mac 1 antibodies.
Figure 6:
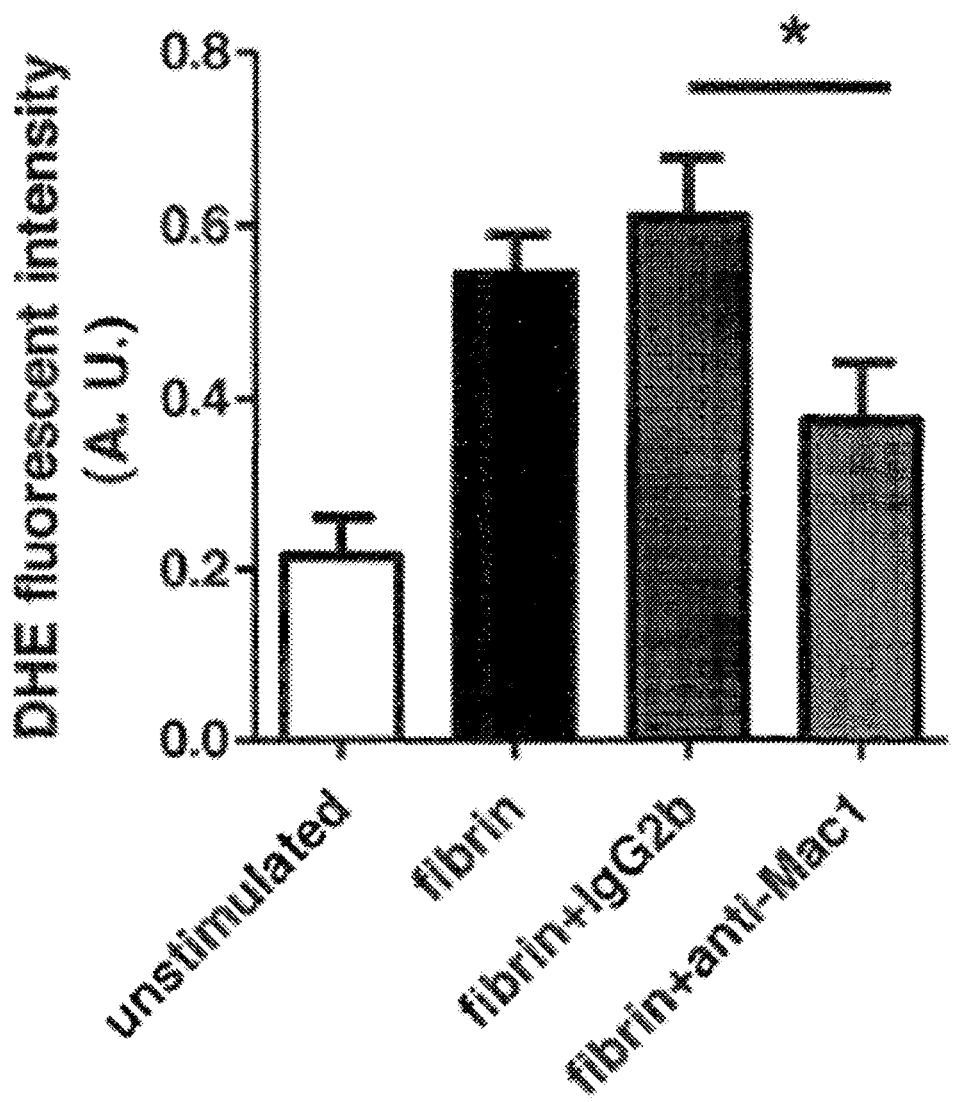
FIG. 6 is a graph illustrating the levels of reactive oxygen species resulting from DHE oxidation in macrophages after 48 hours exposure to the fibrin composition of the invention, alone or with IgG2b or anti-Mac 1 antibodies.

Approximately 100,000 of each of the three groups of DHE-treated BMDMs—the DHE-treated BMDMs, the DHE-treated BMDMs incubated with IgG2b and the DHE-treated BMDMs incubated with anti-Mac1 (CD11b/CD18)—were plated per well on the fibrin assay plates and the control plate. The results are shown in FIGS. 5 and 6.

Statistical analysis was provided by 1 way ANOVA, using 8 wells/group. Levels of ROS as detected with DHE fluorescence were significantly increased in fibrin-stimulated macrophages. The fibrin incubated BMDMs showed a significantly increased level of ROS production as compared to the BMDMs treated with IgG2b or with anti-Mac1 antibodies 24 hours after plating (FIG. 5). After 48 hours, the fibrin incubated BMDMs continued to demonstrate a significantly increased level of ROS production as compared to the BMDMs treated with anti-Mac1 antibodies 48 hours after plating (FIG. 6).

Example 4: Binding of CD11b Using In Vitro Fibrin Compositions in an In Vitro Reactive Oxygen Species Assay Fibrin and fibrinogen assay plates were created as described in Example 1. These plates were incubated in blocking buffer containing PBS with 5% BSA with 0.05% Tween-20 for 1 hour and sealed with adhesive seal. Following incubation, the plates were washed five times with PBS containing 0.05% Tween-20.

Fibrin or fibrinogen were incubated with 50 µL per well of 10 µM CD11b-I domain, singly biotinylated at the amino-terminus in diluent containing PBS with 0.5% BSA and 0.05% Tween-20, for 2 hours at 37° C. The plates were washed five times with PBS containing 0.05% Tween-20 and incubated with 1 µg/mL HRP-coupled Streptavidin (BD Pharmingen, San Jose, Calif.) diluted 1:1000 in PBS with 0.5% BSA and 0.05% Tween-20 for 1 hour at room temperature. The plates were again washed five times with PBS containing 0.05% Tween-20, and incubated with undiluted TMB/E substrate (Chemicon-Millipore, Temecula, Calif.), typically for 4 to 5 minutes at room temperature. The reactions were stopped by the addition of 100 µl/well of IN HCl. Fluorescence was detected at 450 nm.

Figure 7:
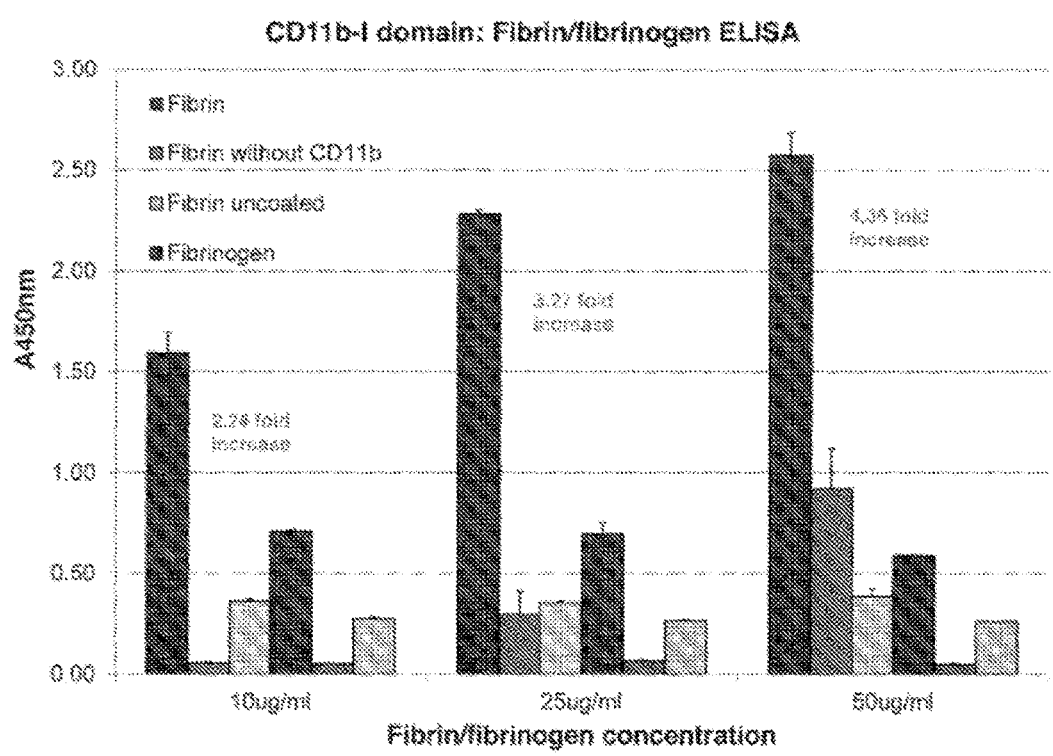
FIG. 7 is a graph illustrating binding of various assay substrates to the proinflammatory fibrin receptor CD11b-I domain using an ELISA assay.
Figure 8:
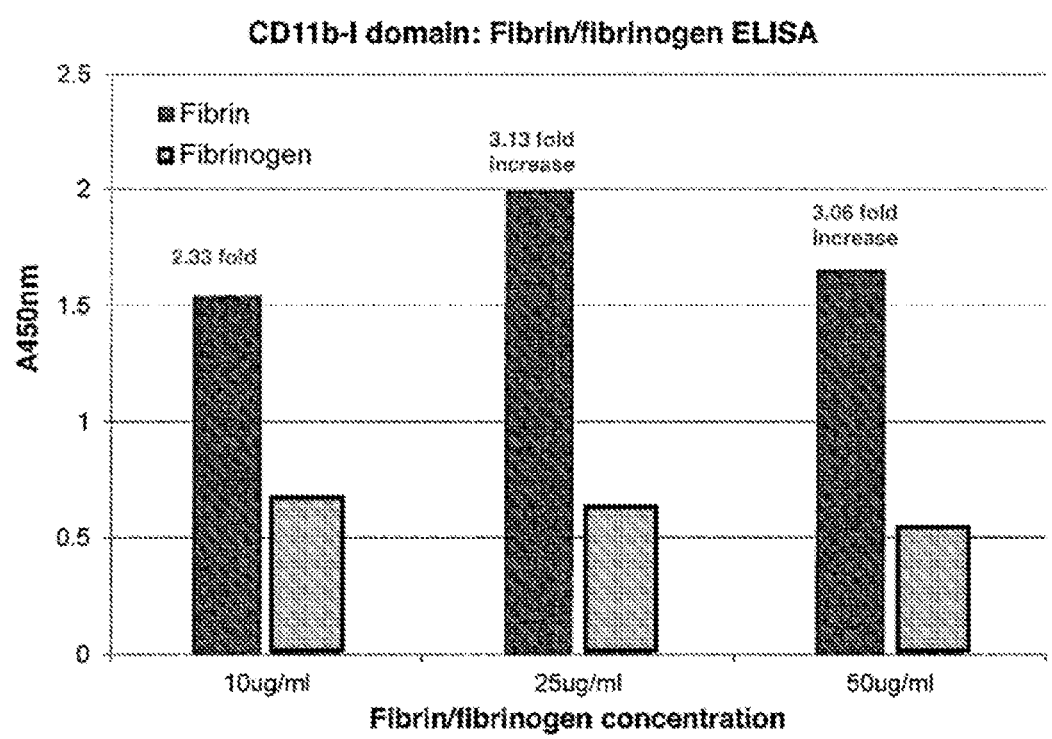
FIG. 8 is a graph illustrating binding of fibrin and fibrinogen to the proinflammatory fibrin receptor CD11b-I domain using an ELISA assay.

This experiment demonstrates a side-by-side comparison of the fibrin compositions and fibrin assay apparatus of the invention compared to in vitro fibrinogen compositions of the invention. Compared to fibrinogen, the fibrin composition substrate exhibits superior binding to the proinflammatory fibrin receptor CD11b-I domain (FIGS. 7 and 8). The exposure of the pro-inflammatory fibrin epitope in vitro provides better prediction of functional results in vivo in the cell-based and test agent binding assays using the compositions and apparatus of the invention.

The experimental results of Example 4 indicate that fibrin assay plates provide an improved substrate for exposure of the CD11b/CD18 epitope, and thus an enhanced functional screening technique for identifying agents that modulate CD11b signaling through fibrin.

The preceding merely illustrates the principles of the invention. It will be appreciated that those skilled in the art will be able to devise various arrangements and equivalents which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. An assay method for identification of test agents that modulate CD11b/CD18 signaling through fibrin, comprising the steps of:
    immobilizing a fibrin composition to a solid support surface, wherein the fibrin composition displays an exposed, pro-inflammatory, cryptic fibrin epitope capable of binding to CD11b/CD18 integrin;
    introducing the test agent to the support surface;
    measuring the binding affinity of the test agent to the fibrin composition immobilized on the solid support surface; and
    identifying agents that exhibit a significant increased binding affinity to the fibrin composition in vitro compared to a control lacking the fibrin composition.

2. A method for identification of a binding partner for modulation of a biological process involving CD11b/CD18 signaling through fibrin, said method comprising:
    providing a research tool composition comprising: a fibrin composition adhered to a solid surface, wherein the fibrin composition comprises an exposed, pro-inflammatory, cryptic fibrin epitope capable of binding to CD11b/CD18 integrin;
    contacting one or more binding partners with the research tool composition; and
    isolating the binding partners that display a significant change in functional activity of the fibrin in the research tool composition;
    wherein the binding partners that display the change in functional activity of the fibrin in the research tool composition are candidate agents for modulation of a biological process involving CD11b/CD18 signaling through the interaction of CD11b/CD18 integrin with fibrin.

3. The method of claim 1, wherein the solid surface comprises glass.

4. The method of claim 1, wherein the solid surface comprises polyethylene, polystyrene or a cyclic olefin polymer substrate.

5. The method of claim 1, wherein the cryptic fibrin epitope is $\gamma_{377\_395}$.

6. The method of claim 1, wherein the immobilizing comprises drying the fibrin composition on the solid support.

7. The method of claim 2, wherein the solid surface comprises glass.

8. The method of claim 2, wherein the solid surface comprises polyethylene, polystyrene or a cyclic olefin polymer substrate.

9. The method of claim 2, wherein the cryptic fibrin epitope is $\gamma_{377\_395}$.

10. The method of claim 2, wherein the providing comprises drying the fibrin composition on the solid support.

11. The method of claim 2, wherein the method further comprises introducing cells that express CD11b/CD18 integrin to the research tool composition.

12. The method of claim 11, wherein the cells introduced to the research tool composition comprise macrophages.

\* \* \* \* \*